US00PP12081P2

(12) United States Plant Patent

Hill, Jr.

(10) Patent No.: US PP12,081 P2

(45) Date of Patent: Sep. 11, 2001

(54) GUZMANIA PLANT NAMED 'SYMFONIE ENCORE'

(76) Inventor: Herbert H. Hill, Jr., 1040 Jameson Rd., Lithia, FL (US) 33547

( * ) Notice: Subject to any disclaimer, the term of this patent is extended or adjusted under 35 U.S.C. 154(b) by 0 days.

(21) Appl. No.: 09/432,079

(22) Filed: Nov. 2, 1999

(51) Int. Cl.[7] ..... A01H 5/00

(52) U.S. Cl. ..... Plt./371

(58) Field of Search ..... Plt./371

(56) References Cited

U.S. PATENT DOCUMENTS

P.P. 9,476 * 3/1996 Kent ..... Plt./371

P.P. 10,069 * 10/1997 Kent ..... Plt./371

P.P. 10,383 * 5/1998 Bos ..... Plt./371

* cited by examiner

*Primary Examiner*—Bruce R. Campell

*Assistant Examiner*—Kent L. Bell

(74) *Attorney, Agent, or Firm*—Foley & Lardner

(57) ABSTRACT

A Guzmania plant named 'Symfonie Encore' characterized by having variegated foliage that is reddish-pink at the sheath becoming cream-white at the apex of the leaf, large and long-lasting inflorescence with a distinctive yellow and red contrast, plants that are resistant to extremes in temperature (38–95° F.) and light intensity thereby tolerating a wide range of cultural conditions.

2 Drawing Sheets

BACKGROUND OF THE INVENTION

The present invention comprises a new and distinct cultivar of Guzmania plant, hereinafter referred to by the cultivar name 'Symfonie Encore'. The genus Guzmania is a member of the family Bromeliaceae.

Guzmania is predominantly epiphytic with a few terrestrial species and is native to the tropics. For the most part, species vary in diameter from 7 or 8 inches to 3 or 4 feet and have rosettes of glossy, smooth-edged leaves.

Floral bracts of Guzmania frequently have brilliant colors and may last for many months. The range of colors for Guzmania is generally from yellow through orange but may also include flame red and red-purple. White or yellow, tubular, three-petalled flowers may also appear on a stem or within the leaf rosette but are usually short-lived.

Guzmania may be advantageously grown as pot plants for greenhouse or home use. Desirably, the plants are shaded from direct sunlight, and during the spring to autumn period, the central vase-like part of the leaf rosette is desirably filled with water.

Guzmania is native to tropical America. Leaves of Guzmania are usually formed as basal rosettes, which are stiff and entire and in several vertical ranks. Guzmania plants have terminal spikes or panicles which are often bracted with petals united in a tube about as long as the calyx. The ovary is superior and the seeds plumose.

Asexual propagation of Guzmania is frequently done through the use of tissue culture practices. Propagation can also be from offshoots produced by the plant which may then be rooted. The resulting plantlets are detached from the mother plant and may be potted in a suitable growing mixture.

Methods for cultivation and crossing of Guzmania are well known. For a detailed discussion, reference is made to the following publications, which are incorporated herein by reference: Benzing, David H., THE BIOLOGY OF THE BROMELIADS, Mad River Press, Inc., Eureka (1980); Zimmer, Karl, BROMELIEN, Verlag Paul Parey, Berlin (1986); and Rauh, Werner, BROMELIEN, Verlag Eugen Ulmer, Stuttgart (1981).

The new cultivar was discovered as a naturally occurring mutation among plants of the parent cultivar 'Symfonie', which is a non-variegated Guzmania plant. The female parent of 'Symfonie' was *Guzmania lingulata* var. *Splendens*. The male parent of 'Symfonie' was *Guzmania zahnii*. 'Symfonie Encore' was discovered and selected among plants of the cultivar 'Symfonie' by the inventor, Herbert H. Hill, Jr., in 1982, in Lithia, Fla.

'Symfonie Encore' is characterized by its medium to large plant size and its variegated leaves that are reddish-pink at the sheath becoming cream-white at the apex. The inflorescence is tall, large and brightly colored yellow and red.

The first act of asexual reproduction of the new cultivar was performed by the inventor in 1982, from offshoots produced by the plant. Horticultural examination of these asexually reproduced plants initiated in 1982 has demonstrated that the combination of characteristics as herein disclosed for 'Symfonie Encore' are firmly fixed and reproduces true to type through successive generations asexual reproduction.

BRIEF DESCRIPTION OF THE INVENTION

The following traits have been repeatedly observed and are determined to be basic characteristics of 'Symfonie Encore' which in combination distinguish this Guzmania as a new and distinct cultivar:

1. Variegated foliage that is reddish-pink at the sheath becoming cream-white at the apex of the leaf;
2. Large, long-lasting inflorescence with a distinctive yellow and red contrast;
3. Plants that are resistant to extremes in temperature (38–95° F.) and light intensity thereby tolerating a wide range of cultural conditions; and 4. Easy, distinctly fast-growing variegated cultivar with few cultural problems.

'Symfonie Encore' has not been observed under all possible environmental conditions. The phenotype of the new cultivar may vary significantly with variations in environment such as temperature, light intensity, and daylength without any change in genotype.

Of the many commercial cultivars known to the inventor, the most similar in comparison to 'Symfonie Encore' are the cultivars 'Symfonie' (unpatented) 'Siralbert' (U.S. Plant patent application Ser. No. 09/419,916). 'Symfonie Encore' differs from 'Symfonie' because 'Symfonie Encore' has variegated foliage. 'Symfonie Encore' and 'Siralbert' both have variegated foliage and yellow and red inflorescence. The plants of 'Symfonie Encore' grow taller and larger than those of 'Siralbert'. 'Symfonie Encore' has a wider leaf-sheath, longer leaf-length and wider leaf-blade than 'Siralbert'. The leaf variegation of 'Symfonie Encore' is distinctly wider than 'Siralbert'. The leaves of 'Symfonie Encore' are erect with a well-defined droop at the last 11–18 cm of the blade. 'Siralbert' has erect arching leaves with no droop. The inflorescence of 'Symfonie Encore' is taller, straighter and has more intensely contrasting color than 'Siralbert'. 'Symfonie Encore' is a faster, stronger and more robust cultivar with fewer cultural problems than 'Siralbert'. 'Symfonie Encore' will tolerate a wider range of temperature and light conditions than 'Siralbert'. 'Symfonie Encore' is a distinctly fast-growing variegated cultivar with few cultural problems. 'Symfonie Encore' is not sensitive to the fungal disease Fusarium, its root system is strong and the plant is quite vigorous when compared to other variegated Guzmania plants. In a growing time of 9 months, 'Symfonie Encore' outgrows Guzmania 'Siralbert' by 30%. The leaves of 'Symfonie Encore' are strong and despite being variegated, they are not sensitive to spotting caused by cell burst.

BRIEF DESCRIPTION OF THE DRAWING

The accompanying photographic illustrations show a typical 'Symfonie Encore' plant following growth under appropriate growing conditions, which colors being as true as possible with illustrations of this type.

Sheet 1 is a side view of the inflorescence and foliage characteristics of 'Symfonie Encore'.

Sheet 2 is a close-up view of the inflorescence of 'Symfonie Encore' showing the distinctive yellow and red contrast.

DETAILED BOTANICAL DESCRIPTION

The following observations, measurements and values describe plants grown in Lithia, Fla., under greenhouse conditions which closely approximate those generally used in horticultural practice. The plant described is approximately 12 months old. Color references are made to The Royal Horticultural Society Colour Chart (R.H.S.), except where general colors of ordinary significance are used.

Classification: Commercial: Guzmania c.v. 'Symfonie Encore'.

Species: Guzmania 'Symfonie Encore' is a variegated form of Guzmania 'Symfonie'; Guzmania 'Symfonie' is a European hybrid. The female parent of 'Symfonie' was *Guzmania lingulata* 'Splendens'.

Parentage: Natural mutation of Guzmania 'Symfonie'.

Propagation: Vegetative, by removal of offsets.

Plant:

*Form.*—Funnel-form rosette.

*Height.*—Approximately 50–65 cm when flowering.

*Diameter.*—Approximately 80–100 cm.

*Growth habit.*—Vigorous, it takes approximately 13 months to produce a finished flowering plant from a 25 cm long cutting, in a standard heated greenhouse with temperatures during the day of 20 degrees Celsius, and 18 degrees Celsius at night.

Foliage:

*Habit.*—Arcuate spreading, inconspicuously appressed lepidote throughout.

*Size.*—Approximately 40–50 cm long.

*Leaf sheaths.*—Elliptic shape, margin entire, surface is glabrous, 15 cm long and 8 cm wide; light green (RHS 193A) with reddish striations (RHS 183D); overall suffused with reddish-purple (RHS 63A) (all color designations are for both upper and lower surfaces.)

*Leaf blades.*—Ligulate, margin is entire, surface is glabrous, apex is acute to attenuate, 25–46 mm wide, variegated. The margins have a 5 to 12 mm-wide zone of green (RHS 143A to 144B). The central zone of the leaf has a 15–30 mm-wide linear band that is cream (RHS 4D) to reddish (RHS 53C) in color (all color designations are for both upper and lower surfaces).

*Scape.*—Approximately 30–45 cm long and 1 cm in diameter, reddish-purple (RHS 63C, both upper and lower surfaces).

*Scape bracts.*—Densely imbricate, apex is acute to attenuate, margin entire, surface is glabrous, foliaceous, concealing the scape, arcuate spreading, 25–35 mm wide, variegation similar to the leaves, central zone is reddish-purple (RHS 66B) to red (RHS 46B) (all color designations are for both upper and lower surfaces).

*Number of Leaves.*—30 to 40.

Inflorescence:

*Habit.*—15 cm long and 12–15 cm wide with approximately 20 spirally arranged bracts.

*Primary bracts.*—Elliptic shape, 15–20 per flower, margin is entire, apex is acute to attenuate, 6–10 cm long and 1–2 cm wide, red (RHS 46C), the lowest with light yellow (RHS 2C) striations toward the base (all color designations are for both upper and lower surfaces).

*Branches.*—3–5 cm long and 2–3 cm wide with a 2–5 mm-long stout peduncle, 10–20 flowers densely and polystichously arranged and spreading at appproximately 45° to the main axis.

*Floral bracts.*—1 floral bract per flower, elliptic shape; cucullate apex; margin is entire, approximately 0.5 cm wide; floral bracts are closely folded around the flowers; 25–30 mm long, carinate, yellow (RHS 7B, both upper and lower surfaces).

*Flowers.*—Pedicel: 2–3 mm-long stout pedicel. Sepals: Narrowly elliptic shape, broadly acute apex, sessile base, margin is entire, 1.5–2 cm long, 5 mm wide, fused for 2–3 mm at the base, yellow (RHS 4B) (Both surfaces). Corolla: Erect, semi-tubular, the lobes flaring slightly, 1.5 cm long, 4–5 mm diameter. Petals: Ligulate, obtuse apex, sessile base, margin is entire, 1.5 cm long, 3–5 mm wide, approximately ½ connate, yellow (RHS 7A) (Both surfaces). Buds:

Elliptic shape, approximately 2–2.5 cm long, 4–5 mm diameter, yellow (RHS 15C).

*Duration of Flowers.*—Individual flowers last for one day and the total duration of flowering is approximately 11–12 weeks.

Reproductive organs: 6 stamens per flower, 1 cm long; filaments are white; anthers are yellow (RHS 15C); 1 style per flower, 1 cm long, yellow (RHS 15C).

Other significant characteristics: The inflorescence holds its color for approximately 6–8 months.

Pollen: No known pollen produced.

Fruit: No fruit produced.

Disease/pest resistance/susceptibility: 'Symfonie Encore' is not sensitive to such fungal diseases as fusarium. Not known resistance and/or susceptibility to pests.

Temperature tolerance: 'Symfonie Encore' is more tolerant to the heat and cold than other Guzmania cultivars that only perform well within a temperature range of 60 to 70 degrees Fahrenheit.

I claim:

1. A new and distinct Guzmania plant named 'Symfonie Encore', substantially as illustrated and described herein.

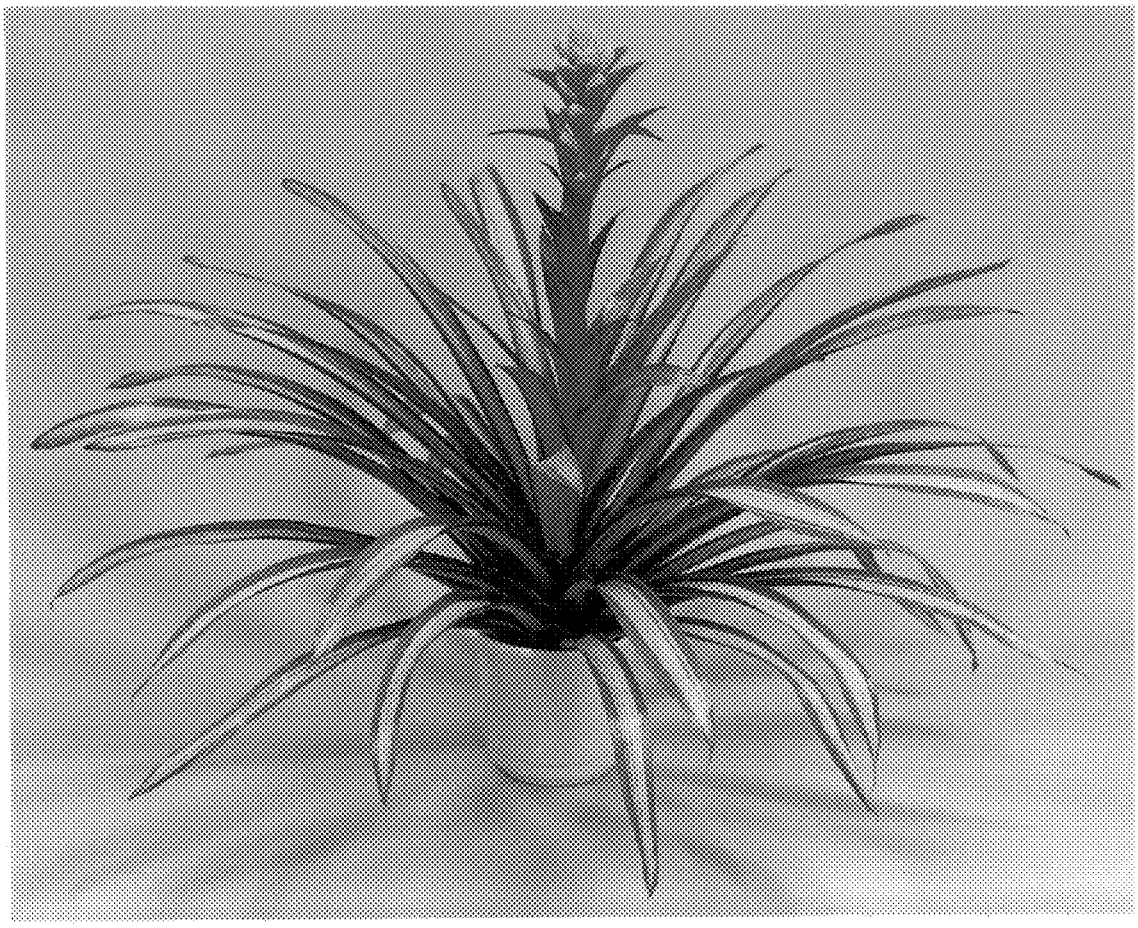

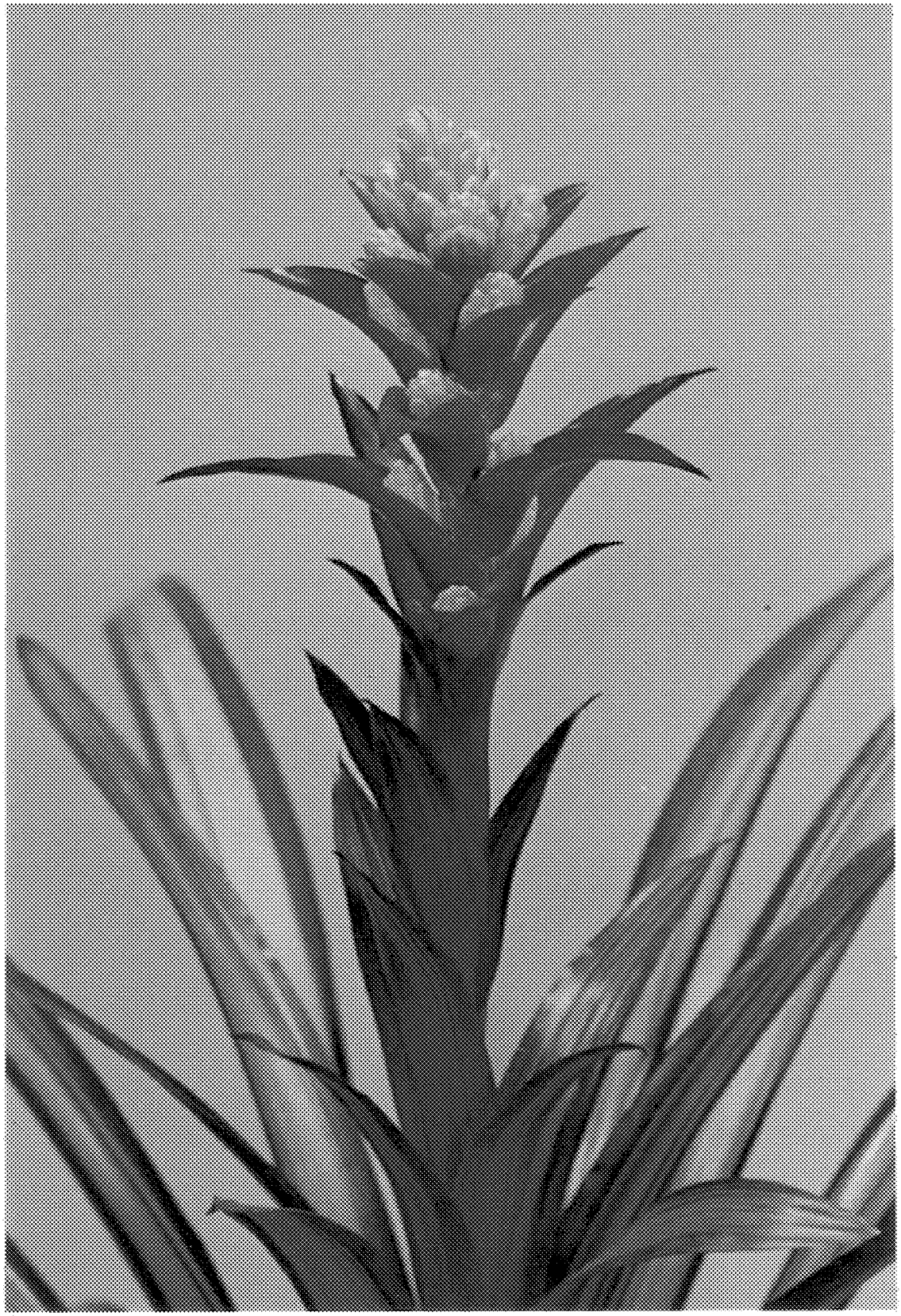

* * * * *